US00PP10614P

United States Patent [19]

Lemon

[11] Patent Number: Plant 10,614

[45] Date of Patent: Sep. 22, 1998

[54] VARIETY OF GERANIUM PLANT NAMED 'ENCHANTMENT'

[75] Inventor: David Lemon, Lompoc, Calif.

[73] Assignee: John Bodger & Sons Company, So. El Monte, Calif.

[21] Appl. No.: 724,680

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,091 1/1993 Walters ..... Plt./87.12

*Primary Examiner*—Howard J. Locker
*Attorney, Agent, or Firm*—Fulwider Patton Lee & Utecht

[57] ABSTRACT

The cultivar is characterized by its compact medium green foliage and pale lavender bloom with dark purple blotches. Its strong growth habit, quick rooting time and continuous flowering provide for superb cuttings and also for quick recovery following wet weather conditions. The blooms are slow to shatter and exhibit good post-harvest quality.

1 Drawing Sheet

BACKGROUND OF THE NEW PLANT

The present invention comprises a new and distinct cultivar of *Pelargonium×domesticum* known by the varietal name Enchantment (Oglevee No. 759, Bodger No. 2 PD 33-5). The new variety was discovered in a selective breeding program by David Lemon at Bodger Seeds, Ltd., Lompac, Calif. The new variety is a selection from the crossing of Princess (U.S. Plant Pat. No. 8,091), which is characterized by a lavender flower with medium green foliage, with Bodger No. 6 PD 23-3 (unpatented). The claimed cultivar is distinguished from the parental cultivars by its richer lavender flower which produces comparatively larger florets and has a faster rooting time.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, and grown in a soiless media of constant fertilizer 150–200 parts per million of nitrogen and potassium has a response time of fourteen weeks from the rooted cutting to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken rooted cuttings believed to have been potted on approximately Feb. 1, 1996 and flowering on approximately Apr. 25, 1996 under full light and greenhouse, and colorings were taken indoors under 200–220 foot candles of fluorescent cool white light using The R.H.S. Colour Chart of The Royal Horticultural Society of London.

The Plant

Classification:
- *Botanical.*—*Pelargonium×domesticum.*
- *Commercial.*—Regal Granium Enchantment.

Form: Upright mound shaped habit.
- *Height.*—26.0–28.0 cm above media surface.
- *Growth.*—Vigorous.
- *Strength.*—Fast rooting, good post-harvest performance.

Foliage: Stalked leaf attachment.

Leaves:
- *Size.*—6.5–8.0 cm.
- *Shape.*—Depressed ovate, truncate base.
- *Margin.*—Serrately lobed.
- *Texture.*—Leathery, slightly pubescent.
- *Color.*—Top: Green group 137B. Bottom: Green group 137C. Zone: Not present.
- *Ribs and veins.*—Palmate venation: Color: Yellow/green group 146D.

Petioles:
- *Length.*—5.5–7.0 cm.
- *Color.*—Yellow/green group 146C.

Stem:
- *Color.*—Yellow/green group 146C.
- *Internodes.*—1.2–3.0 cm.

The Bud (Umbel)

Shape: Elliptical.

Size: 3.0–3.5 cm across; color just beginning to show.

Inflorescence

Blooming habit: Free and early, continuous.

Borne: Umbel; floret on pedicel; pedicel on peduncle.

Closed florets:
- *Bud size.*—1.2–1.5 cm in length, 0.6–0.7 cm wide.
- *Size.*—Fully open bloom: 8.0–9.5 cm across.

Open florets:
- *Form.*—Cupped.
- *Color.*—Top: Violet group 84B; Bottom: Red-purple group 69C. Eye: Grey-purple group 187A with a shading of Red-purple group 74A at the edge of the eye.

*Petals.*—Five.
*Size.*—4.5–5.5 cm across.
*Texture and appearance.*—Satiny. Appearance from a distance in a pale lavender bloom with a dark purple blotch above medium green foliage.

Petaloids:
*Quantity.*—None.

Pedicel:
*Length.*—2.0–3.0 cm.
*Color.*—Yellow-green group 146C.

Peduncle:
*Length.*—5.5–7.0 cm.
*Color.*—Yellow-green group 146B.

Persistence:
*Disease resistance.*—Not known.
*Lasting quality.*—Slow to shatter.

Reproductive Organs

Stamens:
*Anthers.*—3.0 mm in length.
*Filaments.*—Length: 0.7–1.6 cm. Color: White.
*Pollen.*—Golden brown.

Pistils:
*Number.*—One.
*Length.*—1.5–1.9 cm.
*Stigma.*—5–6 parted; Color: Red-purple group 60C.
*Style.*—Length: 1.0–1.2 cm.

Ovaries:
*Color.*—Pale green, pubsecent.
*Length.*—5–6 mm.

Fruit: None.

General Characteristics

Enchantment is a new addition to the Royalty series. The Royalty Series is an easy to grow plant characterized by vigorous upright growth habit, continuous flowering and abundant flowers. When compared to the Princes (U.S. Plant Pat. No. 8,091) variety, which it could replace, Enchantment offers a richer flower color and larger florets while processing similar cutting production and post-harvest performance.

I claim:

1. A new and distinct variety of Geranium plant, substantially as shown and described.

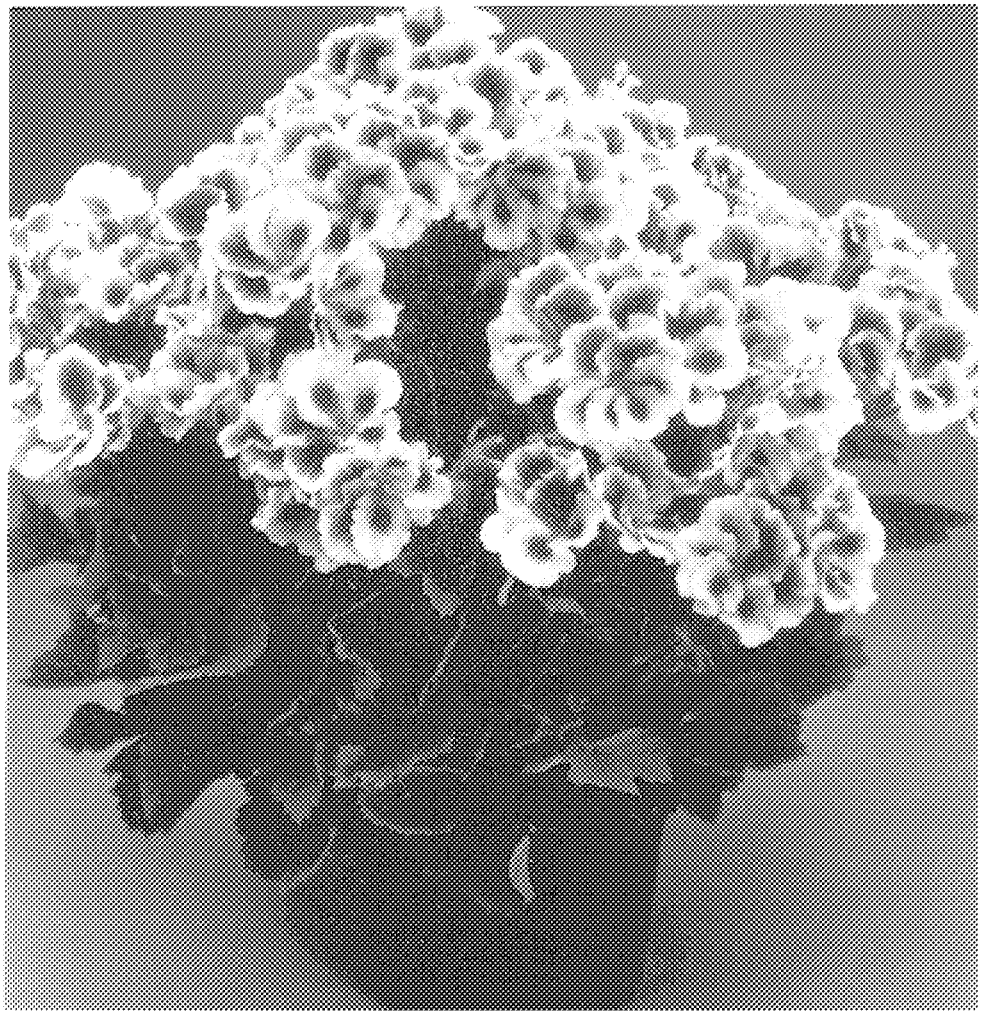

* * * * *